United States Patent [19]

Yoneda

[11] Patent Number: 4,673,812
[45] Date of Patent: Jun. 16, 1987

[54] CALIBRATING MECHANISM OF AN INFRARED ANALYZER

[75] Inventor: Aritoshi Yoneda, Kyoto, Japan

[73] Assignee: Horiba, Ltd., Kyoto, Japan

[21] Appl. No.: 740,056

[22] Filed: May 30, 1985

[30] Foreign Application Priority Data

Jul. 9, 1984 [JP] Japan ............................ 59-143169

[51] Int. Cl.⁴ ...................... G01D 18/00; G01N 21/61
[52] U.S. Cl. ................................ 250/252.1; 250/339; 250/343; 250/345; 250/349
[58] Field of Search ..................... 250/252.1, 339, 343, 250/346, 345, 349

[56] References Cited

U.S. PATENT DOCUMENTS

| 3,562,524 | 2/1971 | Moore et al. | 250/343 |
| 4,040,747 | 8/1977 | Webster | 356/418 |
| 4,346,296 | 8/1982 | Passaro et al. | 250/343 |
| 4,480,190 | 10/1984 | Burough et al. | 250/343 |
| 4,525,069 | 6/1985 | Tanaka et al. | 356/435 |

FOREIGN PATENT DOCUMENTS

3238179A1  4/1984  Fed. Rep. of Germany .
56-58306   5/1981  Japan .

OTHER PUBLICATIONS

"Messen, Steuern und Regeln in der Chemischen Technik", Herausgegeben von, J. Hengstenberg et al., Dritte, neubearbeitete Auflage, New York, 1980, pp. 31-32.

Primary Examiner—Janice A. Howell
Assistant Examiner—Constantine Hannaher
Attorney, Agent, or Firm—Wenderoth, Lind & Ponack

[57] ABSTRACT

An amplifying circuit for amplifying an output from a measurement wavelength detector consists of a preamplifier and a measurement signal amplifier provided at an output of said preamplifier. The measurement signal amplifier is provided with an input-resistance and a feed-back resistance, a variable resistance connected in series to a normally open switch, the series combination being connected in parallel to the feed-back resistance so that the gain of the measurement signal amplifier may be variable.

2 Claims, 2 Drawing Figures

CALIBRATING MECHANISM OF AN INFRARED ANALYZER

BACKGROUND OF THE INVENTION

1. Field of the Invention

The present invention relates to a calibrating mechanism of an infrared analyzer.

2. Description of the Prior Art

In general, it is necessary for an infrared analyzer to carry out the zero-calibration and the span-calibration at regular intervals. Hitherto, a zero-gas is introduced into a measuring cell at the set flow rate and the zero-point is adjusted after the indication was stabilized. Subsequently, a span gas is introduced into the measuring cell at the set flow rate and the span is adjusted after the indication was stabilized. That is to say, the gas-calibrating method has been used. However, this gas-calibrating method has a problem in that an expensive gas which is to be checked with a high accuracy is required at each span-adjustment, so that the calibrating cost is increased.

Contrary to this, a mechanical calibrating method, in which the calibration is easily carried out without usually using a gas by reducing the quantity of light passing through the measuring cell by means of a light-quantity reducer such as a metallic plate, a light-quantity reducing filter or a liquid crystal element to change the quantity of light incident upon the detector, has been tried. However, according to this mechanical calibrating method, where a metallic plate is used as the light-quantity reducer, a subtle influence due to the shift of the inserting position occurs whereby an error is produced. In addition, where the light-quantity reducing filter and the liquid crystal element are used as the light-quantity reducer, the reduction of the light-quantity is changed due to staining, injury, etc. to the light-quantity reducer itself. As described above, it is difficult to hold a high accuracy when using such a mechanical calibrating method. Furthermore, the mechanical calibrating method has a disadvantage in that the trouble is apt to be produced since it includes movable parts.

SUMMARY OF THE INVENTION

It is an object of the present invention to provide a calibrating mechanism of an infrared analyzer capable of easily and accurately carrying out the calibration without requiring the continuous use of a span gas.

An infrared analyzer according to the present invention, in which a measurement signal and a reference signal are separately output and amplified and the difference between the output signals used as an output signal, is characterized by the fact that the span-calibration can be carried out by making the gain of an amplifying circuit for amplifying the measurement signal variable.

According to the present invention, since the span-adjustment is carried out by only making the gain of the amplifying circuit for amplifying the measurement signal variable, the continuous use of an expensive span gas is not required, and furthermore, since the span-drift due to the deterioration of the light source, staining of the cell, etc., may be eliminated, the calibrating cost can be greatly reduced. In addition, since movable parts are not needed, in contradistinction to the mechanical calibration method using a light-quantity reducer therein, the troubles associated therewith are not produced in addition to the significant reduction of the calibrating cost, whereby the calibration can be accurately carried out in spite of the simplicity thereof.

DESCRIPTION OF THE PREFERRED EMBODIMENTS

Figure 1:
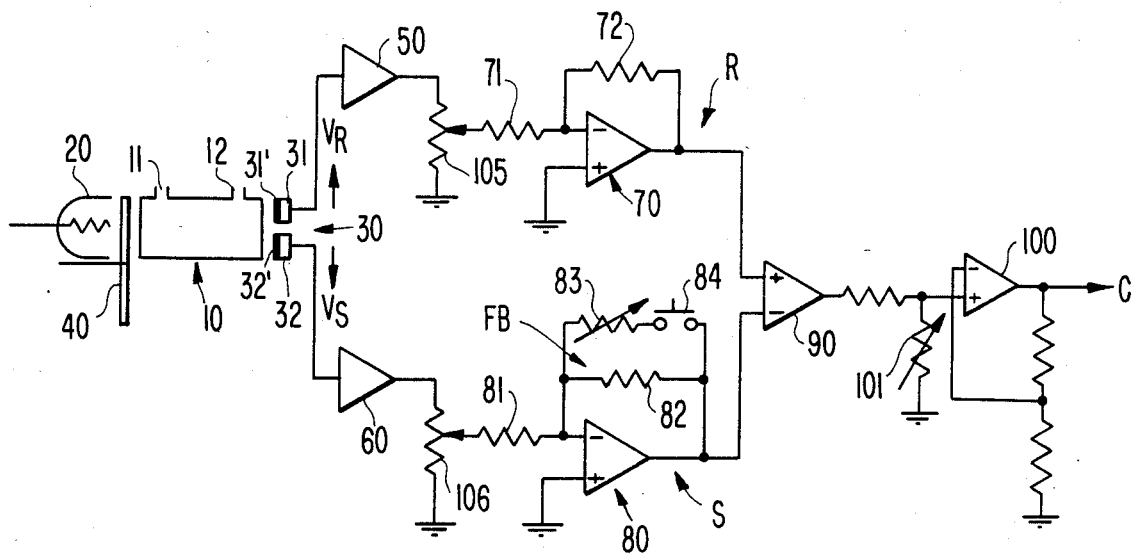
FIG. 1 is a circuit diagram showing a preferred embodiment of an infrared analyzer according to the present invention.

The preferred embodiment of the present invention will be below described with reference to the drawings. Referring now to FIG. 1, which shows an outlined construction of an infrared analyzer of the "one light source-one cell type", element (10) is a cell provided with a sample gas inlet port (11) and a sample gas outlet port (12). Element (20) is a light source for radiating infrared rays and is arranged at one end of the cell (10). Element (30) is a detecting portion arranged at the other end of the cell (10). Element (40) is a modulation-chopper disposed between the cell (10) and the light source (20).

The detecting portion (30) consists of a reference wavelength detector (31) and a measurement wavelength detector (32). The measurement wavelength detector (32) is provided with a bandpass filter (32'), through which infrared rays having wavelengths within the range of the specified absorption band absorbed by the specified ingredient which is to be determined in the sample gas passes, and the detector (32) outputs a measurement signal $V_s$. The reference wavelength detector (31) is provided with a bandpass filter (31'), through which infrared rays having no absorption band for the specified ingredient or having the absorption of an ignorable extent for the specified ingredient passes, and the detector (31) outputs a reference signal $V_R$. Elements (50) and (60) are preamplifiers. Element (70) is a reference-signal amplifier disposed at an output of the preamplifier (50) and is provided with an input resistance (71) and a feed-back resistance (72) for amplifying the reference signal $V_R$ through the preamplifier (50) from the reference wavelength detector (31) at the appointed gain and whose output is fed to a ⊕ input terminal of a subtractor (90). Element (80) is a measurement-signal amplifier disposed at an output of the preamplifier (60) and is provided with an input resistance (81) and a feedback resistance (82) for amplifying the measurement signal $V_s$ through the preamplifier (60) from the measurement wavelength detector (32) at the appointed gain and whose output is fed to a ⊖ input terminal of the subtractor (90). In addition, a variable resistance (83) connected in series with a normally open switch (84) may be connected in parallel with the feedback resistance (82). In short, a feed-back circuit FB is constructed so that the gain of the measurement-signal amplifier (80) may be freely changed. However, the resistance (83) may not always be a variable resistance but may be a fixed resistance. Element (100) is an amplifier disposed at an output of the subtracter (90), and element (101) is a span resistor, and C designates an output of the system.

In the measurement of the concentration of the sample gas, the sample gas is introduced into the cell (10) under the condition that the normally open switch (84) is opened. Infrared rays from the light source (20) are radiated through the sample gas, and the modulation of the infrared rays is carried out by means of the chopper (40). The measurement-signal $V_s$ detected by the measurement wavelength detector (32) and the reference-signal $V_R$ detected by the reference wavelength detector (31) are suitably amplified and then a concentration-signal C is obtained by subtracting the latter from the former.

Figure 2:
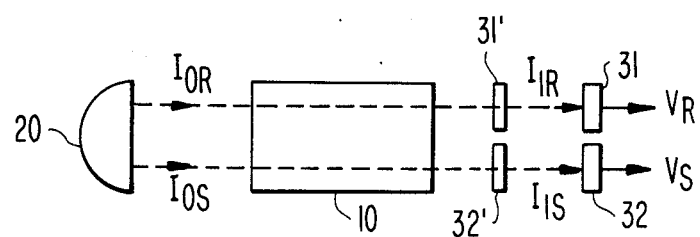
FIG. 2 is a partial block diagram for explaining the operation of FIG. 1.

Next, the span-adjustment of the infrared analyzer constructed in the above described manner will be described with reference to FIG. 1 and FIG. 2.

Referring now to FIG. 1, $I_o$ designates a total gain of a reference electrical system R extending from the preamplifier (50) to an output terminal of the reference-signal amplifier (70), and $I_1$ designates a total gain of a measurement electrical system S extending from the preamplifier (60) to an output terminal of the measurement-signal amplifier (80), and $k_1$ designates a gain of a non-inverting amplifier (100). In addition, referring to FIG. 2, $I_{OR}$ designates the energy of infrared rays included in infrared rays radiated from the light source (20) and having the reference wavelength, and $I_{OS}$ designates the energy of infrared rays included in infrared rays radiated from the light source (20) and having the measurement wavelength. $I_{1R}$ designates the energy of infrared rays having the reference wavelength after passing through the cell (10) and the bandpass filter (31'), and $I_{1S}$ designates the energy of infrared rays having the measurement wavelength after passing through the cell (10) and the bandpass filter (32').

The concentration-signal C from the amplifier (100) is expressed by the following equation (1):

$$C = k_1(I_o V_R - I_1 V_s) \quad (1)$$

Now, provided that a constant proportional to the detecting sensitivity of the reference wave length detector (31) and a constant proportional to the detecting sensitivity of the measurement wavelength detector (32) are $a_1$ and $a_2$, respectively, the reference-signal $V_R$ and the measurement-signal $V_s$ are expressed as follows:

$$V_R = a_1 I_{1R}.$$

$$V_s = a_2 I_{1S}$$

Here, the total gain $I_o$ of the reference electrical system R and the total gain $I_1$ of the measurement electrical system S are adjusted under the condition that the zero gas flows through the cell (10) so that the following equation is satisfied:

$$k_1(I_o V_{RZ} - I_1 V_{SZ}) = 0,$$

wherein $V_{RZ}$ and $V_{SZ}$ are output signals from the reference wavelength detector (31) and the measurement wavelength detector (32), respectively, under the condition that the zero gas flows through the cell (10).

Accordingly, the change of a ratio of $I_{1S}$ to $I_{1R}$ is expressed in the form of a zero-drift. On the other hand, the span-drift is produced only when $I_{1S}$ and $I_{1R}$ are changed by the same ratio or the cell-length and the measurement wavelength are shifted from the optimum value thereof. Although it is difficult to check the correction of the latter as long as the span-gas doesn't flow, the correction of the former can be checked by allowing the zero-gas to flow.

At this juncture, when the span-gas flows, C is expressed by the following equation (2):

$$C = k_1(I_o V_{RS} - I_1 V_{SS}) \quad (2)$$

wherein $V_{RS}$ and $V_{SS}$ are output signals from the reference wavelength detector (31) and the measurement wavelength detector (32), respectively.

But, since $V_{RS}$ is nearly equal to $V_{RZ}$, the equation (2) can be expressed by the following equation (3):

$$C = k_1(I_o V_{RZ} - I_1 V_{SS}) \quad (3)$$

Here, the gain m of the feed-back circuit FB of the measurement-signal amplifier (80) in the span-adjusting process is set to the value less than 1 by closing the switch (84) to reduce the total feed-back resistance. If the adjustment is carried out so that the equation $V_{SS} = m \cdot V_{SZ}$ is satisfied, the above described equation (3) is expressed by the following equation (4):

$$C = k_1(I_o V_{RZ} - m I_1 V_{SZ}) \quad (4)$$

Accordingly, if the gain $m = V_{SS}/V_{SZ}$ is given to $V_{SZ}$ in the span-adjusting process, the signal, which is same as that obtained under the condition that the span-gas flows, can be obtained under the condition that the zero-gas flows.

Now, provided that $I_{1R}$ and $I_{1S}$ are changed by the same ratio a, the concentration-signal C can be expressed by the following equation (5):

$$C = k_1(I_o a V_{RS} - I_1 a V_{SS}) = a k_1(I_o V_{RS} - I_1 V_{SS}) \quad (5)$$

Since, on the other hand, the correct value of the span is $k_1(I_o V_{RS} - I_1 V_{RS})$, and is found from the comparison of the right side of equation (5) with this correct value of the span that the former is a times the latter, that is to say, the span-drift is produced.

Described below is how this span-drift can be adjusted by the present invention. Provided that $I_{1R}$ and $I_{1S}$ are checked under the condition that they are changed by the same ratio a, the following equation (6) is satisfied:

$$C' = k_1(I_o a_1 V_{RZ} - m I_1 a V_{SZ}) = a k_1(I_o V_{RZ} - m I_1 V_{SZ}) = a k_1(I_o V_{RS} - I_1 V_{SS}) \quad (6)$$

This equation (6) is identical with the above described equation (5). That is to say, the state, which is smae as that obtained under the condition that the span-gas flows, can be reproduced by only changing the gain of the measurement-signal amplifier (80) without requiring the flow of the span-gas. If the reduction of the quantity of light due to the deterioration of the light source (20) is compensated (so that $a = 1$ is satisfied) by means of the span-variable resistor (101) under this condition, the former correct value of the span can be obtained.

One example of the practical adjustment is described below.

At first, the zero-calibration is carried out by adjusting variable resistors (105) and (106) with the zero-gas flowing so that the signal quantity of the reference electrical system R may be equal to that of the measurement electrical system S and an output of the subtracter (90) becomes zero. Then, the span variable resistor (101) is adjusted with the span-gas of a known concentration flowing so that an output of a meter connected to C reads that concentration. Under this condition, that is to say, the condition that the zero-calibration and the span-calibration have been completely carried out, the zero-gas flows without delay and the normally open switch (84) is closed after the stabilization of the indication. The value of the indication at this time is stored. Where the resistance (83) is a variable resistance, the resistance (83) is changed so that the value of the indication becomes a suitable value.

In the subsequent periodical checking processes, the zero-calibration is carried out with the zero-gas flowing and then the normally open switch (84) closed with the zero-gas continuously flowing so as to adjust the span variable resistor (101) so that the value of the indication may become the stored value.

Although an infrared analyzer of the "one light source-one cell" type was described in the above described preferred embodiment, the present invention is not limited thereto. For example, the present invention can be applied also to an infrared analyzer of the "two-cell" type in which a reference cell is arranged in parallel with a sample cell. In addition, the present invention can be applied also to a "multi-component analyzer". In short, the present invention can be applied to every analyzer of the type in which a reference-signal and a measurement-signal are individually output and the difference between the two signals output as a concentration-signal.

What is claimed is:

1. A calibrating mechanism of an infrared analyzer having a reference wavelength detector connected to a reference signal amplifier and a measurement wavelength detector connected to a measurement signal amplifier, outputs of said two amplifiers being subtracted so as to generate an analyzer output, said mechanism comprising a gain adjusting means connected to said measurement amplifier for setting a gain thereof at one of a first and a second value, wherein, when said gain adjusting means sets the gain of said measurement amplifier to said first value, a zero calibration is effected with a zero gas flowing through said analyzer and a span calibration is effected with a span gas flowing through said analyzer and wherein, when said gain adjusting means sets the gain of said measurement amplifier to said second value, said analyzer output with said zero gas flowing through said analyzer is equal to said analyzer output with said span gas flowing through said analyzer when the gain of said measurement amplifier was set at said first value, such that said analyzer may be subsequently recalibrated using only said zero gas.

2. A mechanism as recited in claim 1, wherein said measurement amplifier includes an operational amplifier having a feedback resistance and said gain adjusting means comprises a series combination of a normally open switch connected in series with a variable resistance, said series combination being connected in parallel with said feedback resistance, said variable resistance being adjusted so as to adjust said gain of said measurement amplifier to said second value.

* * * * *